Dec. 20, 1955 C. G. DUEHRSEN Plant Pat. 1,441
ROSE PLANT
Filed Nov. 16, 1954
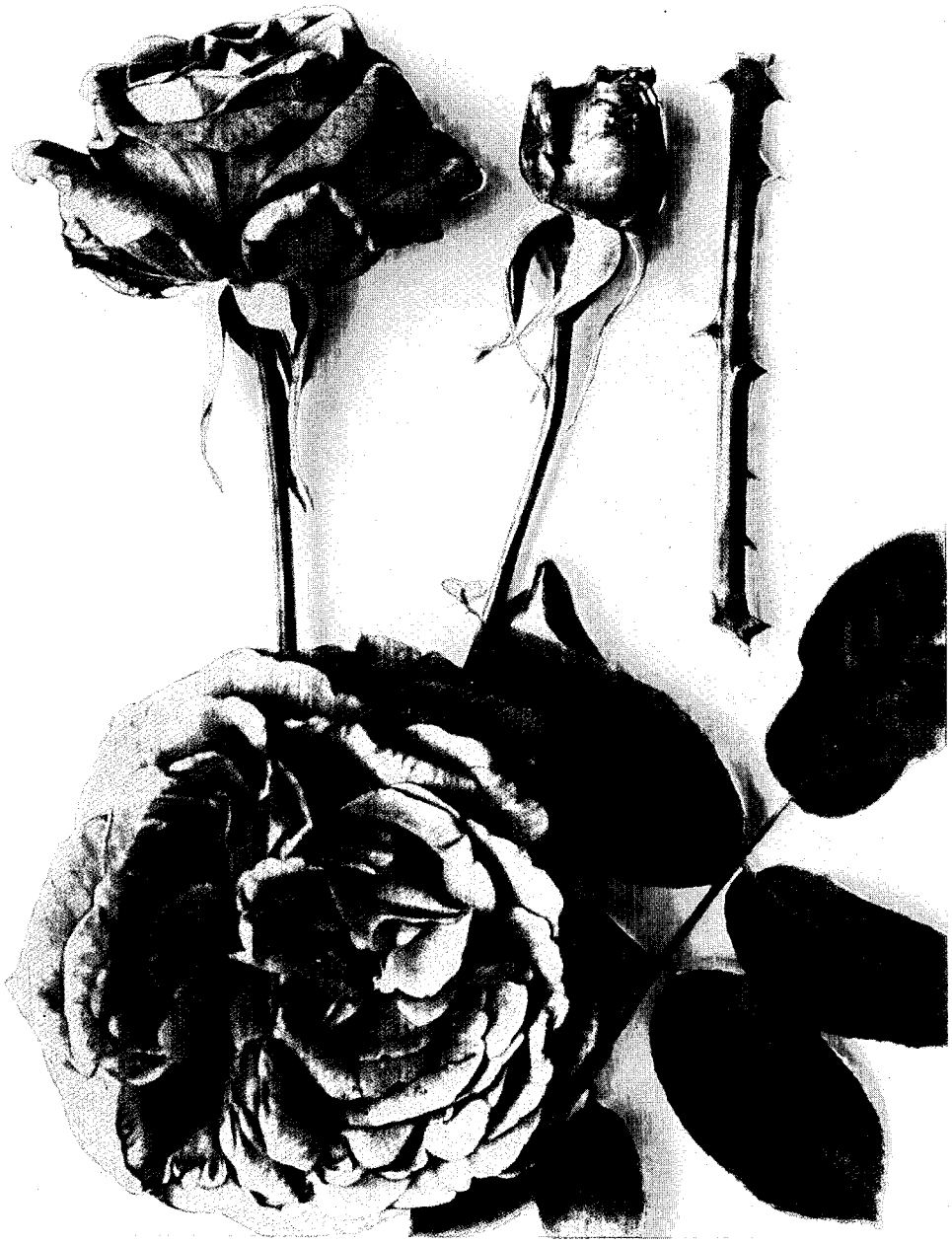
INVENTOR
Carl George Duehrsen
By Orville M. Kile
Plant Patent Agt United States Patent Office Plant Pat. 1,441

Patented Dec. 20, 1955

1,441

ROSE PLANT

Carl George Duehrsen, Montebello, Calif., assignor to Howard & Smith, Inc., Montebello, Calif.

Application November 16, 1954, Serial No. 469,282

1 Claim. (Cl. 47—61)

My present invention relates to a new and improved variety of hybrid tea rose plant in the class producing dark red blooms. It originated as a seedling whose parentage is Red Talisman (Plant Patent No. 59) × Southport (unpatented) × Mirandy (Plant Pat. No. 632). The crosses were made by me at my home property in Montebello, where I do considerable hybridizing of roses in an effort to obtain improved varieties.

The new variety has been reproduced asexually by me from buds, at Montebello, and its outstanding characteristics appear to be permanent.

Accompanying illustrations show the side view of a bud, the top view of a fully opened flower, a typical leaf, and a portion of stem with thorns, all in approximately their true colors.

In the following detailed description of my new variety, color plate references indicate Ridgway's Color Standards and Nomenclature, and where color names are used without plate reference the ordinary dictionary meaning is intended.

THE PLANT

Class: Hybrid tea rose.

Growth habit: Healthy and strong-growing, upright bush which attains an average height of 3 to 5 feet.

*Blooming habit.*—Season is 8 to 9 months in Southern California and the plant produces a good quantity of blooms throughout the season.

Stem: Strength above the average. Length about 15 inches. Color dark green but almost entirely covered with brown which is between Hay's Brown (Pl. XXXIX) and Garnet Brown (Pl. 1). Many thorns occur on the lower portion.

*Thorns.*—Almost horizontal, but slightly reclining. Average length is ¼ inch. Color Oxblood Red (Pl. I).

Foliage:

*Type.*—Odd pinnate, usually with 5 to 7 leaflets.

*Shape.*—Ovate, with acuminate apex.

*Size.*—Terminal leaflet approximately 1½ inches by 2½ inches.

*Texture.*—Coriaceous.

*Quantity.*—Moderate.

*Color.*—Dark green, approximately Yew Green (Pl. XXXI).

*Aspect.*—Glossy. Mid-vein prominent.

*Rachis.*—Slender; grooved above.

*Stipules.*—Not prominent.

*Disease resistance.*—During three years' testing no mildew has been noticed on this new variety even though other varieties alongside of it have been contaminated with mildew at different times of the year. No blackspot or other disease has been seen, but are not particularly prevalent on other varieties in this area.

THE FLOWER

Bud:

*Size.*—Averages 1¼ inches in length just before unfolding.

*Shape.*—Semi-globular.

*Color.*—Oxblood Red (Pl. I).

*Peduncle.*—Short, about 1½ inches long.

*Sepals.*—Long but simple. Measures 1½ inches in length by slightly less than a half inch in width at base.

Bloom:

*Borne.*—Singly in most cases.

*Size.*—Large, with usual flowers 4 to 5½ inches across and a depth of 1¾ inches.

*Form.*—Applanate, centre remaining covered.

*Petalage.*—Usually 35 to 40 petals.

*Color.*—Outer petals Pomegranate Purple (Pl. XII), shading to Oxblood Red (Pl. I) in center of flower.

*Fragrance.*—More than average amount of usual rose fragrance.

*Longevity.*—Average.

Petals:

*Shape.*—Cuneate, with edges slightly wavy and entire except for slight notch at top.

*Substance.*—Heavy.

*Size.*—Average 2 inches by 1¾ inches.

Reproductive organs:

*Pistils.*—Number aggregated. *Style* ¼ inch long, Nopal Red (Pl. I). *Stigma* Salmon Orange (Pl. II).

*Stamens.*—Average number 35. *Filaments* ½ inch long, Nopal Red (Pl. I). *Anthers* medium in size. Salmon Orange (Pl. II).

*Receptacle.*—Prominent; embossed; Lemon Yellow (Pl. IV).

COMPARISON

One of the varieties that this new variety is somewhat similar to is the variety Major Shelly (Pl. Pat. 447), but it differs in a number of points, principal of which are as follows:

1. The color of the flower of my new variety is much darker and of a different tone of red.
2. My variety is a much stronger grower and in three years' testing has been resistant to mildew although other varieties—including Major Shelly—when grown alongside have at different times had this disease.
3. Although Major Shelly is considered a prolific bloomer, my new variety is a much freer bloomer.
4. Its flowers are more fragrant than those of Major Shelly.
5. Its stems are stronger and are brown instead of the green of those of Major Shelly.
6. Foliage is shaped differently—my variety has leaves that are not so pointed.
7. Its bud is shorter and less pointed.
8. Its open flower has a fuller appearance and different form.

Having thus disclosed my invention, I claim:

The new and distinct variety of hybrid tea rose plant, substantially as herein shown and described, characterized particularly by its bloom of dark red color and applanate form, in combination with its strong growth and disease resistance; its strong, brown stems; its pleasant and plentiful rose fragrance; and its free blooming habit throughout a long season.

No references cited.